United States Patent [19]

Iwao et al.

[11] 4,224,457
[45] Sep. 23, 1980

[54] PROCESS FOR MANUFACTURING OPTICALLY ACTIVE SULFUR-CONTAINING CARBOXYLIC ACID

[75] Inventors: Jun-ichi Iwao, Hyogo; Masayuki Oya, Higashi; Eishin Kato; Toshio Watanabe, both of Osaka, all of Japan

[73] Assignee: Santen Pharmaceutical Co., Ltd., Osaka, Japan

[21] Appl. No.: 35,836

[22] Filed: May 4, 1979

[30] Foreign Application Priority Data

May 18, 1978 [JP] Japan .................................. 53/59678

[51] Int. Cl.³ .............................................. C07B 19/00
[52] U.S. Cl. .................................... 562/401; 562/426; 562/578; 562/594
[58] Field of Search ................ 562/401, 426, 578, 594

[56] References Cited

U.S. PATENT DOCUMENTS

| | | | |
|---|---|---|---|
| 3,600,437 | 8/1971 | Marshall | 562/401 |
| 3,686,183 | 8/1972 | Dyson | 562/401 |
| 3,739,019 | 6/1973 | Ueda et al. | 562/401 |
| 3,758,559 | 9/1973 | Bollinger | 562/401 |
| 3,794,655 | 2/1974 | Schubel et al. | 562/401 |
| 3,803,213 | 4/1974 | Weber et al. | 562/401 |
| 3,904,683 | 9/1975 | Day et al. | 562/401 |
| 4,111,987 | 9/1978 | Schmidt et al. | 562/401 |

*Primary Examiner*—Natalie Trousof
*Assistant Examiner*—Vera C. Clarke
*Attorney, Agent, or Firm*—Frishauf, Holtz, Goodman & Woodward

[57] ABSTRACT

Process for manufacturing optically active sulfur-containing carboxylic acid which comprises reacting a racemic acid of the formula

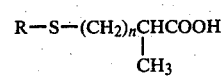

$$R-S-(CH_2)_n\underset{CH_3}{\overset{|}{C}}HCOOH$$

with an optically active amine to form the amine salt, and then resolving the isomers and recovering the optically active isomer.

17 Claims, No Drawings

PROCESS FOR MANUFACTURING OPTICALLY ACTIVE SULFUR-CONTAINING CARBOXYLIC ACID

DETAILED EXPLANATION OF THE INVENTION

This invention relates to a process for manufacturing important optically active sulfur-containing carboxylic acids useful in the preparation of mercapto-substituted amino acid derivatives and other useful optically active compounds which have pharmacological effects such as antihypertensive effect, etc. In other words, this invention relates to a process for manufacturing optically active sulfur-containing carboxylic acid which comprises reacting racemic sulfur-containing carboxylic acid of the formula

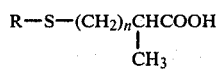

wherein
n is 0 or 1;
R is hydrogen, benzoyl, acetyl or benzyl;
with an optically active amine, and subjecting the resulting amine salts to fractional crystallization for optical resolution and for convertion to free acid.

Optically active compounds of the formula [I] are novel compounds, which have been separated from each racemic mixture for the first time by the inventors.

Up to now, racemic sulfur-containing carboxylic acid itself is used as the material of the above medicine, etc. The obtained compound was racemic mixture or mixture of diastereoisomers in some cases and it was difficult to obtain the optically pure and active objective compound. By the use of optically active sulfur-containing carboxylic acid obtained by the method of this invention, the above difficulty is solved and the desired optically active compound can be directly obtained.

The practice of this invention comprises dissolving racemic sulfur-containing carboxylic acid in acetone, ethanol, chloroform, benzene, isopropyl ether, etc., adding the optically active amine such as brucine, quinine, strychnine, quinidine, cinchonidine, cinchonine, (S)-(−)-or (R)-(+)-α-phenylethylamine, (R)-(−)- of (S)-(+)-1,2-diphenylethylamine and dehydroabiethylamine, etc., and subjecting the resulting salts of the formula [I] to fractional crystallization and conversion to free acid for optical resolution of the racemic acid.

The preferable result is obtained in the following case. When n is 1 in the formula [I], (R)-(−)-1,2-diphenylethylamine, (S)-(+)-1,2-diphenylethylamine, quinine or dehydroabiethylamine preferably should be used for the above optically active amine, and acetone for the solvent. When n is 0 in the formula [I], cinchonine or cinchonidine preferably should be used for the optically active amine, and acetone or ethanol for solvent. The above amine salt is converted to (+)- or (−)-free acid by the known method. Examples are shown below.

EXAMPLE 1

105 g of (±)-S-benzoyl-2-mercaptopropanoic acid is dissolved in 600 ml of ethanol and heated to reflux. To this solution, 147 g of cinchonine is added and dissolved thoroughly, and cooled overnight. The obtained crystals are collected on a filter and dried, yield 86.5 g.

These crystals are recrystallized from 200 ml of ethanol to give 47.4 g of (S)-(−)-S-benzoyl-2-mercaptopropanoic acid cinchonine salt, mp. 166°-167° C., $[\alpha]_D^{25}+123.2°$ (c=1.0, methanol).

By the known method, the above obtained salt is converted to (S)-(−)-S-benzoyl-2-mercaptopropanoic acid, yield 18.7 g (35.6%), mp. 63°-65° C., $[\alpha]_D^{25}-69.9°$ (c=2.5, methanol).

EXAMPLE 2

The salt in the filtrate obtained in Example 1 is converted to free acid by the known method, yield 67.5 g, $[\alpha]_D^{25}+15.0°$ (c=1.0, methanol). The acid is dissolved in 970 ml of acetone and heated to reflux. To this solution, 94.5 g of cinchonidine is added, dissolved thoroughly, and allowed to stand overnight at room temperature. The produced crystals are collected on a filter and dried to give cinchonidine salt, yield 75.6 g. This salt is recrystallized from 900 ml of acetone to give (R)-(+)-S-benzoyl-2-mercaptopropanoic acid cinchonidine salt, yield 52.8 g, mp. 153°-157° C., $[\alpha]_D^{25}-72.3°$ (c=2.0, methanol).

By the known method, this salt is converted to (R)-(+)-S-benzoyl-2-mercaptopropanoic acid, yield 21.2 g (40.4%), mp. 63°-66.5° C., $[\alpha]_D^{25}+70.0°$ (c=1.5, methanol).

EXAMPLE 3

67.3 g of (±)-S-benzoyl-3-mercapto-2-methylpropanoic acid is dissolved in 900 ml of acetone and heated to reflux. To this solution, 94.8 g of dehydroabiethylamine is added, dissolved thoroughly, and cooled overnight. The produced crystals are collected on a filter and dried. The obtained dehydroabiethylamine salt is recrystallized twice from acetone to give (S)-(−)-S-benzoyl-3-mercapto-2-methylpropanoic acid dehydroabiethylamine salt, yield 19.1 g, mp. 158°-158.5° C., $[\alpha]_D^{25}+1.1°$ (c=2.0, methanol).

By the known method, this salt is converted to (S)-(−)-S-benzoyl-3-mercapto-2-methylpropanoic acid, yield 7.1 g (21.1%), mp. 68°-71° C., $[\alpha]_D^{25}-38.1°$ (c=2.1, methanol).

EXAMPLE 4

68.7 g of (±)-S-benzoyl-3-mercapto-2-methylpropanoic acid is dissolved in 400 ml of acetone and heated to reflux. To this solution, 60.4 g of (R)-(−)-1,2-diphenylethylamine is added and cooled overnight. The produced crystals are collected on a filter and dried to give (R)-(−)-1,2-diphenylethylamine salt, yield 64.7 g. This salt recrystallized from 190 ml of acetone to give (S)-(−)-S-benzoyl-3-mercapto-2-methylpropanoic acid (R)-(−)-1,2-diphenylethylamine salt, yield 38.2 g, mp. 135.5°-136° C., $[\alpha]_D^{25}-75.3°$ (c=1.6, methanol).

By the known method, this salt is converted to (S)-(−)-S-benzoyl-3-mercapto-2-methylpropanoic acid, yield 21.3 g (62.1%), mp. 69°-71.5° C., $[\alpha]_D^{25}-40.4°$ (c=2.0, methanol).

EXAMPLE 5

The salt in the filtrate obtained in Example 4 is converted to free acid by the known method, yield 35.2 g, $[\alpha]_D^{25}+20.3°$ (c=1.4, methanol).

The acid is dissolved in 630 ml of acetone and heated to reflux. To this solution, 51.0 g of quinine is added, dissolved thoroughly, and cooled overnight. The produced crystals are collected on a filter and dried to give 68.9 g of quinine salt. This salt is recrystallized twice from acetone to (R)-(+)-S-benzoyl-3-mercapto-2-methylpropanoic acid quinine salt, yield 37.9 g, mp. 132°–133° C., $[\alpha]_D^{25}$ −99.5° (c=1.1, methanol).

By the known method, this salt is converted to (R)-(+)-S-benzoyl-3-mercapto-2-methylpropanoic acid, yield 15.0 g (43.7%), mp. 68°–71° C., $[\alpha]_D^{25}$ +39.3° (c=2.4, methanol).

EXAMPLE 6

5.0 g of (±)-S-benzyl-3-mercapto-2-methylpropanoic acid is dissolved in 35 ml of acetone and heated to reflux. To this solution, 4.7 g of (R)-(−)-1,2-diphenylethylamine is added and cooled overnight. The produced crystals are collected on a filter and dried to give (R)-(−)-1,2-diphenylethylamine salt, yield 5.1 g. This salt is recrystallized from 20 ml of acetone to give (S)-(−)-S-benzyl-3-mercapto-2-methylpropanoic acid (R)-(−)-1,2-diphenylethylamine salt, yield 3.3 g, mp. 122°–123° C., $[\alpha]_D^{25}$ −55.6° (c=1.4, methanol).

By the known method, this salt is converted to (S)-(−)-S-benzyl-3-mercapto-2-methylpropanoic acid, yield 1.2 g (48.0%), bp. 152° C. (0.4 mmHg), $[\alpha]_D^{25}$ −28.0° (c=2.4, methanol).

EXAMPLE 7

To 4.4 g of (S)-(−)-S-benzoyl-3-mercapto-2-methylpropanoic acid obtained in Example 4, 50 ml of conc. ammonia is added and stirred at room temperature for 1.5 hours. Ammonia is removed in vacuo and the mixture is extracted with ethyl acetate. The organic layer is washed with saturated sodium chloride solution, dried over anhydrous magnesium sulfate, and distilled in vacuo to give (S)-(−)-3-mercapto-2-methylpropanoic acid, yield 2.19 g (92.8%), bp. 91° C. (3 mmHg), $[\alpha]_D^{25}$ −26.6° (c=3.0, methanol).

EXAMPLE 8

8.1 g of (±)-S-acetyl-3-mercapto-2-methylpropanoic acid is dissolved in 35 ml of acetone and heated to reflux. To this solution, 9.9 g of (R)-(−)-1,2-diphenylethylamine is added and cooled overnight. The produced crystals are collected on a filter and dried to give (R)-(−)-1,2-diphenylethylamine salt, yield 3.9 g. This salt is recrystallized from 40 ml of acetone to give (S)-(−)-S-acetyl-3-mercapto-2-methylpropanoic acid (R)-(−)-1,2-diphenylethylamine salt, yield 2.6 g, mp. 166°–168° C., $[\alpha]_D^{25}$ +16.5° (c=1.1, methanol).

What we claim is:

1. A process for manufacturing optically active sulfur-containing carboxylic acid which comprises reacting a racemic acid of the formula

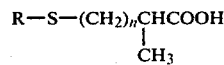  [I]

wherein n is 0 or 1;

R is hydrogen, benzoyl, acetyl or benzyl;

with an optically active amine selected from the group consisting of brucine, quinine, strychnine, quinidine, cinchonidine, cinchonine, (S)-(−)- or (R)-(+)-α-phenyl-ethylamine, (R)-(−)- or (S)-(+)-1,2-diphenylethylamine and dehydroabiethylamine to form the amine salt of said racemic acid in a resolution solvent, and fractionally crystallizing to separate the optically active isomers of said amine salts, and converting said optically active isomers of said amine salts to the optically active acid isomers.

2. The process of claim 1 wherein n is 1, and wherein said optically active amine is selected from the group consisting of (R)-(−)-1,2-diphenylethylamine, (S)-(+)-1,2-diphenylethylamine, quinine and dehydroabiethylamine.

3. The process of claim 2 wherein said resolution solvent is acetone.

4. The process of claim 1 wherein n is 0, and wherein said optically active amine is cinchonine or cinchonidine.

5. The process of claim 4 wherein said resolution solvent is acetone or ethanol.

6. The process of claim 1 wherein said racemic acid is (±)-S-benzoyl-2-mercaptopropanoic acid.

7. The process of claim 6 wherein said optically active amine is cinchonine and wherein said resolution solvent is ethanol.

8. The process of claim 6 wherein said optically active amine is cinchonidine and wherein said resolution solvent is acetone.

9. The process of claim 1 wherein said racemic acid is (±)-S-benzoyl-3-mercapto-2-methylpropanoic acid.

10. The process of claim 9 wherein said optically active amine is dehydroabiethylamine and wherein said resolution solvent is acetone.

11. The process of claim 9 wherein said optically active amine is (R)-(−)-1,2-diphenylethylamine and wherein said resolution solvent is acetone.

12. The process of claim 9 wherein said optically active amine is quinine and wherein said resolution solvent is acetone.

13. The process of claim 1 wherein said racemic acid is (±)-S-benzyl-3-mercapto-2-methylpropanoic acid.

14. The process of claim 13 wherein said optically active amine is (R)-(−)-1,2-diphenylethylamine and wherein said resolution solvent is acetone.

15. The process of claim 1 wherein said racemic acid is (±)-S-acetyl-3-mercapto-2-methylpropanoic acid.

16. The process of claim 15 wherein said optically active amine is (R)-(−)-1,2-diphenylethylamine and wherein said resolution solvent is acetone.

17. The process of claim 1 wherein one of said optically active acid isomers in which R is benzoyl, acetyl or benzyl is reacted with ammonia to produce the corresponding optically active acid isomer wherein R is hydrogen.